(12) United States Patent
Sato et al.

(10) Patent No.: US 7,971,484 B2
(45) Date of Patent: Jul. 5, 2011

(54) METHOD FOR EVALUATING RELIABILITY OF STEEL AND HIGH-RELIABILITY STEEL OBTAINED BY THE SAME

(75) Inventors: Kaiko Sato, Hyogo (JP); Misaki Nagao, Hyogo (JP); Kazuhiko Hiraoka, Hyogo (JP); Ichiro Takasu, Hyogo (JP); Yasukasu Unigame, Hyogo (JP)

(73) Assignee: Sanyo Special Steel Co., Ltd., Hyogo (JP)

( * ) Notice: Subject to any disclaimer, the term of this patent is extended or adjusted under 35 U.S.C. 154(b) by 698 days.

(21) Appl. No.: 11/918,784

(22) PCT Filed: Apr. 18, 2006

(86) PCT No.: PCT/JP2006/308506
§ 371 (c)(1),
(2), (4) Date: Dec. 12, 2007

(87) PCT Pub. No.: WO2006/120875
PCT Pub. Date: Nov. 16, 2006

(65) Prior Publication Data
US 2009/0126492 A1   May 21, 2009

(30) Foreign Application Priority Data
May 10, 2005   (JP) ................................. 2005-137787

(51) Int. Cl.
*G01M 13/04* (2006.01)
(52) U.S. Cl. .............................. 73/593; 73/602; 73/622
(58) Field of Classification Search .................... 73/593, 73/602, 622, 159, 614, 597, 598, 599, 609, 73/610, 620, 627
See application file for complete search history.

(56) References Cited

U.S. PATENT DOCUMENTS

| | | | | |
|---|---|---|---|---|
| 3,495,958 A | * | 2/1970 | Talmage | 75/243 |
| 6,065,343 A | * | 5/2000 | Kiuchi et al. | 73/622 |
| 6,318,178 B1 | | 11/2001 | Kato et al. | |
| 6,474,163 B1 | * | 11/2002 | Takada et al. | 73/600 |
| 7,207,223 B2 | * | 4/2007 | Narai et al. | 73/593 |

(Continued)

FOREIGN PATENT DOCUMENTS
EP   1 475 633   11/2004
(Continued)

OTHER PUBLICATIONS

International Search Report mailed on Jul. 24, 2006 for International Application No. PCT/JP2006/308506 of which the present application is the U.S. National Stage.

(Continued)

*Primary Examiner* — Jacques M Saint Surin
(74) *Attorney, Agent, or Firm* — Wenderoth, Lind & Ponack, L.L.P.

(57) ABSTRACT

A method for evaluating the reliability of steel in terms of inclusions is characterized in that the inclusions of approximately 100 μm or less in maximum inclusion size are evaluated by microscopy combined with the extreme-value statistical analysis; the inclusions of approximately 100 μm or greater in maximum inclusion size are evaluated by the ultrasonic flaw detection testing performed at a frequency of 5 to 25 MHz; and the reliability of the steel is evaluated based on the results of the extreme-value statistical analysis applied to the results of the microscopy and the results of the ultrasonic flaw detection testing combined.

16 Claims, 7 Drawing Sheets

U.S. PATENT DOCUMENTS

| | | | |
|---|---|---|---|
| 7,608,130 B2 * | 10/2009 | Sakamoto et al. | 75/570 |
| 7,615,099 B2 * | 11/2009 | Sakamoto et al. | 75/570 |
| 2006/0048576 A1 | 3/2006 | Kiuchi et al. | |

FOREIGN PATENT DOCUMENTS

| | | |
|---|---|---|
| JP | 6-2073 | 1/1994 |
| JP | 2000-30922 | 1/2000 |
| JP | 2000-144230 | 5/2000 |
| JP | 2000-144330 | 5/2000 |
| JP | 2001-26836 | 1/2001 |
| JP | 2001-141704 | 5/2001 |
| JP | 2001-279373 | 10/2001 |
| JP | 2001-342512 | 12/2001 |
| JP | 2001-342515 | 12/2001 |
| JP | 2001-342516 | 12/2001 |
| JP | 2003-232367 | 8/2003 |
| JP | 2003-247046 | 9/2003 |
| JP | 2003-329653 | 11/2003 |
| JP | 2004-045095 | 2/2004 |
| JP | 2004-093227 | 3/2004 |
| JP | 2004-144289 | 5/2004 |
| JP | 2004-177168 | 6/2004 |
| WO | 03/060507 | 7/2003 |

OTHER PUBLICATIONS

Written Opinion of the International Searching Authority mailed on Jul. 24, 2006 for International Application No. PCT/JP2006/308506 of which the present application is the U.S. National Stage.

Kato, Yoshiyuki et al., "Recent evaluation procedures of nonmetallic inclusions in bearing steels (statistics of extreme value method and development of higher frequency ultrasonic testing method)" ASTM Spec Tech Publ; ASTM Special Technical Publication 2002, No. 1419, May 8, 2001, pp. 176-194.

Zhang, J M et al., "Estimation of maximum inclusion size and fatigue strength in high-strength ADF1 steel" Materials Science and Engineering A: Structural Materials: Properties, Microstructure & Processing, Lausanne, Ch, vol. 394, No. 1-2, Mar. 15, 2005, pp. 126-131.

International Preliminary Report on Patentability mailed Nov. 22, 2007 for International Application No. PCT/JP2006/308506.

Written Opinion of the International Searching Authority mailed Nov. 22, 2007 for International Application No. PCT/JP2006/308506.

Hiroyuki Kondo, "Recent Advantages of Evaluation Methods for Non-metallic Inclusions in Steel", Tetsu-to-Hagane, 2004, pp. 8-16, with partial translation.

Yoshiyuki Kato et al., "Recent Evaluation Procedures of Nonmetallic Inclusions in Bearing Steels (Statistics of extreme value method and development of higher frequency ultrasonic testing method)", Sanyo Technical Report vol. 8 (2001), No. 1, pp. 59-68, with partial translation.

K. Tsubota et al., "Effect of Inclusion Size on Rolling Life Span," Proceedings of the Society of Materials Science of Japan, vol. 46, pp. 105-106 (1997), with English translation.

\* cited by examiner

METHOD FOR EVALUATING RELIABILITY OF STEEL AND HIGH-RELIABILITY STEEL OBTAINED BY THE SAME

TECHNICAL FIELD

The present invention relates to a method for evaluating the reliability of steel and high-reliability steel obtained by such a method. More particularly, the present invention relates to a method for evaluating the reliability of steel that employs microscopy combined with extreme-value statistical analysis and ultrasonic flaw detection testing ("Ultrasonic flaw detection testing" is used as a synonym of "Ultrasonic testing"), to detect the presence of inclusions of several to several hundred μm in size, and also relates to high-reliability steel obtained by such a method. The microscopy combined with the extreme-value statistical analysis allows estimation of the size of the largest inclusions in steel by statistical analysis of the size of inclusions observed by microscopy. The ultrasonic flaw detection testing detects flaws at a detection frequency of 5 to 25 MHz.

BACKGROUND ART

Increasing the rolling contact fatigue life is essential to achieving high reliability of bearings. It is well known that the life of bearings is significantly affected by non-metallic inclusions. Rolling contact fatigue life is classified into two types depending on the required reliability. One is known as the $L_{10}$ life that serves as a common measure of bearing performance, and the other is known as the short life that is determined based on accidental failures. Specifically, the term "short life" is defined as the length of bearing life at which a bearing fails prematurely, or earlier than its calculated life span. Since the $L_{10}$ life and the short life are determined based on two different types of failures that occur at significantly different frequencies, the difference in the frequency of these failures is thought to be due to inclusions occurring at significantly different frequencies. Accordingly, a proper inspection volume for inclusion evaluation (reliability evaluation) must be selected depending upon the type of inclusions, or the type of bearing life.

The $L_{10}$ life of bearings is considered to be determined by small- or medium-sized inclusions, specifically inclusions of approximately 100 μm or less in size (primarily several to several tens of microns). The short life of bearings is considered to be determined by large inclusions sized approximately 100 μm or greater. Thus, a system needs to be constructed that can evaluate the two types of inclusions and can thus be used to define high-reliability steel.

Techniques conventionally used to evaluate the cleanliness of steel are microscopy designed for the evaluation of non-metallic inclusions in steel as specified in JIS G0555, microscopy designed for the direct observation of polished specimens using a microscope as specified in ASTM E45, and the acid-solution technique, in which diluted $HNO_3$ or the like is used to dissolve iron matrix to extract the inclusions from steel for observation.

One technique commonly used to detect inclusions present in steel is the ultrasonic flaw detection technique. Patent Document 1 describes a rolling element of a power roller bearing in which the maximum size of the inclusions present in the element at twice the depth of the maximum shear stress position or lesser depths is limited to 200 μm or less.

Patent Document 2 describes a high-cleanliness steel in which the number of 20 μm or larger oxide inclusions detected by acid-dissolving of the steel is 40 or less per 100 g of the steel.

Patent Document 3 describes steel with stable heat treatment distortion in which it is ensured that the number of inclusions that have a $\sqrt{AREA}$ of greater than 100 μm is 2 or less per $1.0 \times 10^5$ mm$^3$ of the steel.

Patent Document 4 describes a technique in which test specimens are prepared by rolling and/or forging a steel at a rolling and/or forging ratio of 6 or higher and normalizing or annealing the steel and are then subjected to water-immersed ultrasonic flaw detection using a point focused-type probe at a frequency of 5 to 25 MHz to detect the inclusions in the steel. The technique achieves improved detection accuracy.

| | |
|---|---|
| [Patent Document 1] Publication No. 2004-144289 | Japanese Patent Laid-Open |
| [Patent Document 2] Publication No. 2001-342512 | Japanese Patent Laid-Open |
| [Patent Document 3] Publication No. 2003-247046 | Japanese Patent Laid-Open |
| [Patent Document 4] Publication No. 2004-93227 | Japanese Patent Laid-Open |

DISCLOSURE OF THE INVENTION

Problems to be Solved by the Invention

Although the technique described in Patent Document 1 is directed to inclusions with maximum inclusion size of 200 μm or less, the description does not mention anything concerning evaluation of large inclusions on the basis of materials.

A drawback of the technique of Patent Document 2 is that, although the technique requires certain specifications for inclusions in the material, it can achieve only low reliability since the evaluation of large inclusions must rely on the extraction by the acid-solution process, which cannot detect B-type inclusion clusters. B-type inclusions, as defined in JIS G 0555, are aggregates of (more than three) black or bluish particles having multiple non-deformable angles and having a low aspect ratio (typically less than 3). These inclusions are aligned in the direction of deformation.

The methods described in Patent Documents 3 and 4 are suitable for the evaluation of large inclusions, but not appropriate for the evaluation of small- or medium-sized inclusions.

The present invention is intended to address the above-described conventional problems and it is thus an object of the invention to provide a method for evaluating reliability of steel that can determine the total reliability over the entire size range of different inclusions that can affect the fatigue life and other properties of steel.

It is another object of the present invention to provide highly reliable steels selected by the inspection procedure that allows determination of the total reliability over the entire size range of different inclusions that can affect the fatigue life and other properties of steel.

Thus, the present invention provides a method for evaluating reliability of steel, characterized in that inclusions of approximately 100 μm or less in maximum inclusion size are evaluated by microscopy combined with the extreme-value statistical analysis; inclusions of approximately 100 μm or greater in maximum inclusion size are evaluated by a ultrasonic flaw detection testing performed at a frequency of 5 to 25 MHz; and the reliability of the steel is evaluated based on the results of the extreme-value statistical analysis applied to the results of the microscopy and the results of the ultrasonic flaw detection testing performed at a frequency of 5 to 25 MHz combined.

The present invention also provides a high-reliability steel having high reliability in terms of inclusions present therein, the steel obtainable through the selection by an evaluating method (inspection process) for evaluating reliability of steel, including evaluating inclusions of approximately 100 μm or less in maximum inclusion size by microscopy combined with the extreme-value statistical analysis; evaluating inclusions of approximately 100 μm or greater in maximum inclusion size by a ultrasonic flaw detection testing performed at a frequency of 5 to 25 MHz; and evaluating the reliability of the steel based on the results of the extreme-value statistical analysis applied to the results of the microscopy and the results of the ultrasonic flaw detection testing performed at a frequency of 5 to 25 MHz combined.

DESCRIPTION OF THE REFERENCE NUMERALS

| 10 | ultrasonic flaw detector |
|---|---|
| 11 | point focused-type probe |
| 12 | ultrasonic flaw detection unit |
| 13 | scanning unit |
| 14 | PC (personal computer) |
| 15 | visualization unit |
| 20 | test specimen |
| 21 | evaluation region |
| 22 | "porosity" region |
| 23 | end region |
| 24 | non-sensitive region |
| 25 | peripheral region |
| 26 | detection range |
| B | specimen width |
| D | specimen outer dimension (diameter of billet) |
| WP | distance in water |
| MP | focal depth |
| $F_1$ | focal point (in test specimen) |
| $F_2$ | focal point (in water) |

DETAILED DESCRIPTION OF THE INVENTION

The method for evaluating the reliability of steel according to an embodiment of the present invention will now be described in detail with reference to the accompanying drawings.

Figure 1:
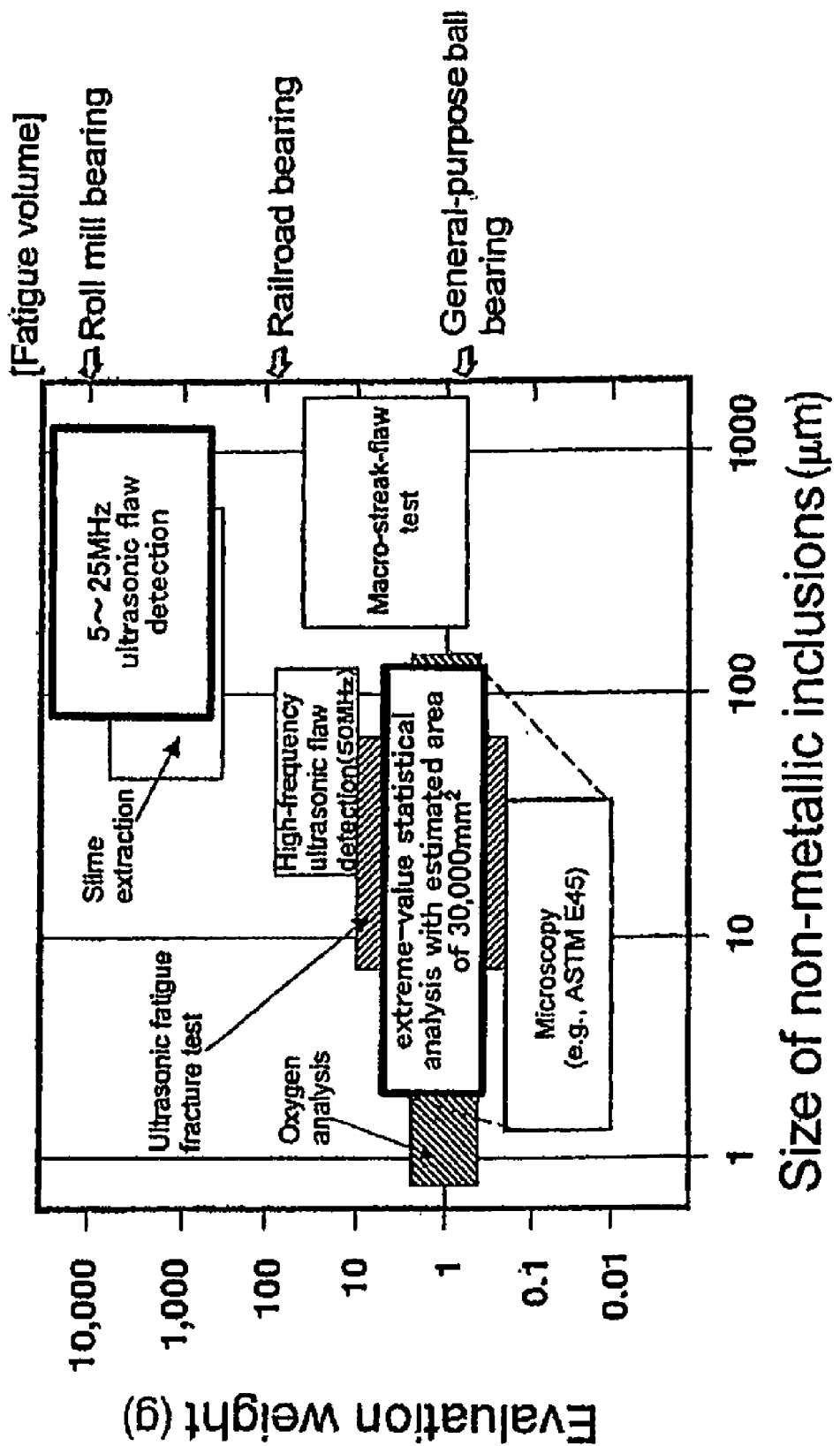
FIG. 1 is a schematic diagram illustrating a scheme for evaluating different types of inclusions in terms of the evaluation weight and the size of the inclusions to be evaluated.

FIG. 1 is a schematic diagram illustrating a scheme for evaluating different types of inclusions in terms of the evaluation volume and the size of the inclusions to be evaluated. In FIG. 1, the evaluation volume is converted into the evaluation weight, and the vertical axis of the diagram shows the evaluation weight.

In the diagram, the evaluation volume for microscopy involving observation of a planar surface and macro-streak-flaw test involving observation of a curved surface, was given by the thickness of inclusions observed on the test surface (set to be 10 μm for ease of understanding) multiplied by the inspection area of the test surface. Using the following equation, the fatigue volume under rolling contact surface was estimated for three types of bearings with different sizes and was shown in the diagram in weight.

(Fatigue volume)=(Hertzian contact area between a rolling element and an inner race)×(depth at 90% of maximum shear stress)

The fatigue volume for each bearing is in the order of 1 g for general-purpose ball bearings, 100 g for railroad bearings, and 10 kg for large rolling mill bearings, varying by a factor of approximately 10,000.

Thus, a method intended for evaluating large inclusions needs to be able to evaluate inclusions not only over a broad size range, but also in large evaluation volumes. The large volume inspection is also necessary because a fatigue volume of 1 g can add up to the order of kilogram if the number of the parts is significantly large.

Different methods for the evaluation of inclusions are described below in the increasing order of inspection volume.

(1) Microscopy

Microscopy techniques used to evaluate inclusions are the techniques according to JIS and ASTM-E45 and the technique combined with extreme-value statistical analysis that can evaluate an increased volume. The evaluation volume of the technique combined with extreme-value statistical analysis is approximately 1 g, an amount close to the fatigue volume of general-purpose ball bearings, while the volume may vary depending on the conditions.

(2) Total Oxygen Analysis

The total oxygen analysis is a relatively simple, effective technique used in the evaluation of the cleanliness for a long time. The technique is still used in comparing product quality. Although the oxygen content is correlated to the $L_{10}$ life, the oxygen analysis is not a direct method and cannot provide information about the size of inclusions.

(3) Macro-Streak-Flaw Test

This test (Method of macro-streak-flaw test for steel: JIS G0556) has a small evaluation area and is thus not practical in the detection of large inclusions.

(4) High-Frequency (50 Mhz) Ultrasonic Flaw Detection Testing

While the high-frequency (50 MHz) ultrasonic flaw detection testing can be used as an alternative to microscopy, it cannot provide sufficient information about chemical composition, size and morphology of inclusions.

(5) Ultrasonic Fatigue Fracture Test

In the ultrasonic fatigue fracture test, specimens are fatigued at a high frequency in the ultrasonic range, and the inclusions exposed on the fracture surface and served as the origins of fracture are directly observed. Unlike most fatigue tests that are time-consuming, the ultrasonic fatigue fracture test is performed at 20 kHz and $10^7$ times repeated load is completed in 10 minutes. The inspection volume for each test specimen is approximately 40 mm$^3$, so that if the test is performed on 20 test specimens, the total inspection weight will be 6 g and if the extreme-value statistical analysis is further used to estimate a volume of 10 times, the total inspection weight will become 60 g. A drawback of the ultrasonic fatigue fracture test is that it can evaluate the specimens only in its transverse cross-sections in an axial load test. To evaluate the cleanliness of steel, specimens must be also evaluated in longitudinal cross-sections since the metal flow can have different directions depending on working process in the fatigue volume of actual bearings. In this aspect, the ultrasonic fatigue fracture test is less favored than microscopy combined with the extreme-value statistical analysis.

(6) Slime Extraction and Acid Extraction

Despite being direct methods to determine the size distribution of inclusions, slime extraction and acid extraction are time-consuming processes. Moreover, the two processes cannot properly evaluate B-type inclusion clusters in large volume tests.

(7) 5 to 25 MHz UT

Although ultrasonic flaw detection testing at a flaw detection frequency of 5 to 25 MHz (referred to as "5 to 25 MHz UT," hereinafter) is effective in the evaluation of steel reliability, it is not an effective approach to evaluating effective life span. However, the 5 to 25 MHz UT is appropriate for detecting rare large inclusions because of its large inspection volume.

The present inventors compared different combinations of the above-described techniques for evaluating inclusions and have found that the extreme-value statistical analysis of the results of microscopy combined with the 5 to 25 MHz UT (preferably 15 MHz UT) is the most effective approach to evaluating inclusions sized several to several hundred µm.

Application of the extreme-value statistical analysis to the results of microscopy enables evaluation of microinclusions over the entire size range of approximately 100 µm or less. The evaluation volume by this approach is as much as 1 g, an amount comparable to the fatigue volume of general-purpose ball beatings, while the evaluation volume may vary depending on the conditions for evaluation. The microscopy combined with extreme-value statistical analysis is effective in evaluating large microinclusions of approximately 100 µm or less in size that determines the rolling contact fatigue life. On the other hand, rare larger inclusions of approximately 100 µm or greater in size that have a size distribution different from small- and medium-sized inclusions cannot be evaluated by microscopy combined with the extreme-value statistical analysis and requires large volume tests (in the order of kg). These large inclusions of approximately 100 µm or greater in size are considered to be effectively evaluated by the ultrasonic flaw detection testing performed at a frequency of 5 to 25 MHz (preferably at 15 MHz) when the detectability and the inspection volume of the technique are considered. By combining "the microscopy combined with extreme-value statistical analysis" and the ultrasonic flaw detection testing, the cleanliness of bearing steel can be adequately evaluated as a measure of the performance and reliability of the steel. As a result, the total reliability of steel can be determined over the entire size range of inclusions. In the evaluation used in the steel making process, the combination of "the microscopy combined with extreme-value statistical analysis" and the ultrasonic flaw detection testing thus facilitates narrowing down the causes of failures.

The method for evaluating the reliability of steel of the present embodiment is characterized in that the microscopic inclusions (oxides, sulfides, and nitrides) are evaluated by microscopy in conjunction with the extreme-value statistical analysis, while larger inclusions are evaluated by the ultrasonic flaw detection testing at a frequency of 5 to 25 MHz.

Figure 2:
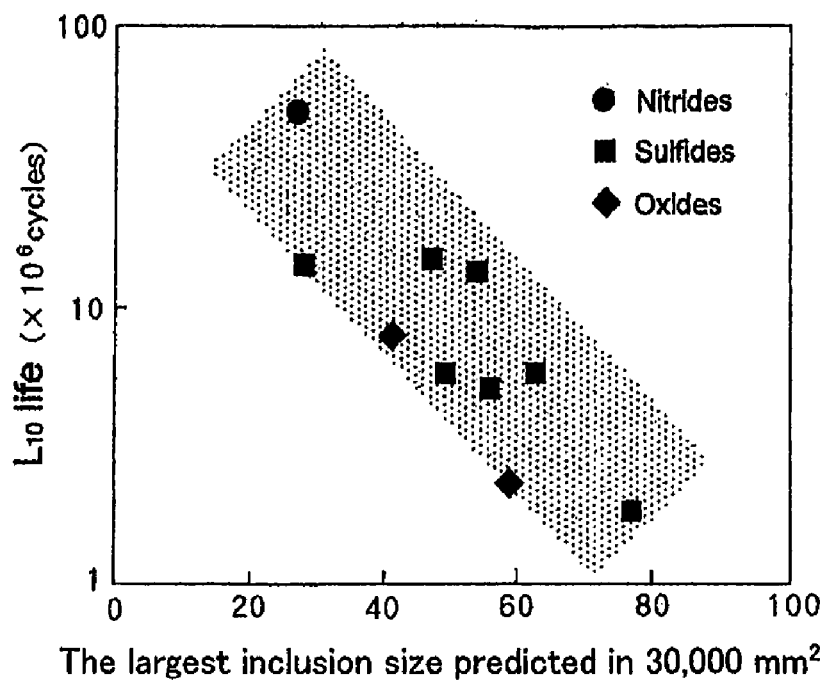
FIG. 2 is a diagram showing the relationship between the maximum inclusion size, estimated by microscopy combined with the extreme-value statistical analysis according to the method for evaluating reliability of steel of the present embodiment, and the rolling contact fatigue life.

FIG. 2 shows the relationship between the estimated maximum inclusion size determined by the microscopy combined with extreme-value statistical analysis for the estimation area S of 30,000 mm$^2$ according to the method for evaluating the reliability of steel of the present embodiment, and the rolling contact fatigue life. $L_{10}$ life shown in FIG. 2 was determined under the following conditions: steel used=JIS SUJ2 (JIS G 4805); test specimens=Φ60×Φ20×t5.8 mm discs prepared by slicing a steel rod in the direction perpendicular to the longitudinal direction; hardness=62HRC; and the tester=thrust-type rolling contact fatigue tester.

FIG. 2 shows the relationship between the $L_{10}$ life and the predicted maximum $\sqrt{AREA}$ value, the square root of the area of the predicted largest inclusion (predicted maximum inclusion size, indicated as $\sqrt{AREA}max$, hereinafter), among the oxide inclusions, sulfide inclusions and nitride inclusions according to the rolling contact fatigue life and the microscopy combined with extreme-value statistical analysis.

It has been shown that the $L_{10}$ life of each test specimen is correlated with the maximum inclusion size of the three types of inclusions. This indicates that the $L_{10}$ life is not determined by the type of the inclusions, but by the maximum inclusion size. The evaluation of the $\sqrt{AREA}max$ of oxides, sulfides and nitrides provides the reliability for the distribution of small- to medium-sized inclusions (the estimated largest inclusion) of approximately 100 µm or less.

The $\sqrt{AREA}$ value, or the square root of the area of an inclusion, is generally determined by the equation $\sqrt{AREA}=\sqrt{(A \times B)}$, where A is the length of an inclusion and B is the width of the inclusion, as determined by microscopy. The direction of the width (B) is perpendicular to the direction of the length (A). Thus, $\sqrt{AREA}$ value serves as a measure of the average size determined by approximating an inclusion to a rectangle.

The $\sqrt{AREA}max$ value is also defined as the $\sqrt{AREA}$ value of the largest inclusion in a given field of view of a microscope (for example, 100 mm$^2$ area), or the $\sqrt{AREA}$ value of the predicted largest inclusion in a prediction field of view.

We now describe the microscopy combined with extreme-value statistical analysis for use in the present invention. In performing a typical microscopy combined with extreme-value statistical analysis, multiple test specimens selected from a given population of specimens from a sample (a steel product) are observed by microscopy to determine the size of the largest inclusion (as measured by the square root of area) present in each specimen. By plotting the size of the largest inclusions on a sheet of extreme probability paper, the size of the largest inclusion (i.e., $\sqrt{AREAmax}$) present in a given population or a given volume (or area) or a prediction volume (or area) can be estimated. Like other methods used in the evaluation of inclusions, the microscopy with combined extreme-value statistical analysis is used to evaluate inclusions in mass-produced materials. In one specific case, 30 non-overlapping fields of view of a microscope, for example each having an area of 10 mm×10 mm (i.e., standard inspection area=$S_0$), are observed for the presence of inclusions for each specimen. Then, the $\sqrt{AREAmax}$ value that indicates the size of the largest inclusion in the estimation area (S=30,000 mm$^2$) is estimated by the extreme-value statistical analysis. The $L_{10}$ life is the length of (rating) life by which 10% of specimens will fail. The relationship between the $\sqrt{AREAmax}$ and the $L_{10}$ life has been determined empirically.

A sample (a steel product) is preferably determined to be highly reliable when the largest inclusion size estimated by the microscopy combined with extreme-value statistical analysis for the standard inspection area $S_0$ of 80 mm$^2$ or larger and the estimation area S of 30,000 mm$^2$ is 50 μm or less since such steel achieves an $L_{10}$ life of $1\times10^6$ cycles as shown in FIG. 2. It has been demonstrated that $L_{10}$ life of $1\times10^6$ cycles ensures long life in other types of steel tested under different conditions.

A sample (steel product) is also preferably determined to be highly reliable when the largest inclusion size estimated by the microscopy combined with extreme-value statistical analysis for the standard inspection area $S_0$ of 80 mm$^2$ or larger and the estimation area S of 30,000 mm$^2$ is 30 μm or less since such steel achieves an $L_{10}$ life of $1\times10^7$ cycles as shown in FIG. 2. It has been demonstrated that $L_{10}$ life of $1\times10^7$ cycles ensures long life in other types of steel tested under different conditions.

By selecting the standard inspection area $S_0$ to be 400 mm$^2$ or larger, the estimation of the largest inclusion size can be stabilized.

The evaluation by microscopy combined with the extreme-value statistical analysis is individually applied to oxide, sulfide, and nitride inclusions since oxides, sulfides, and nitrides have different size distributions and should thus be individually evaluated. Another reason that these inclusions should be individually evaluated is that the estimated largest inclusion sizes of oxide, sulfide, and nitride inclusions tend to become close to one another in ultra-high cleanliness steels, so that the conventional approach, designed to evaluate oxides only, is not effective enough to determine if a given steel has a sufficient reliability in terms of, for example, the $L_{10}$ life.

Figure 3:
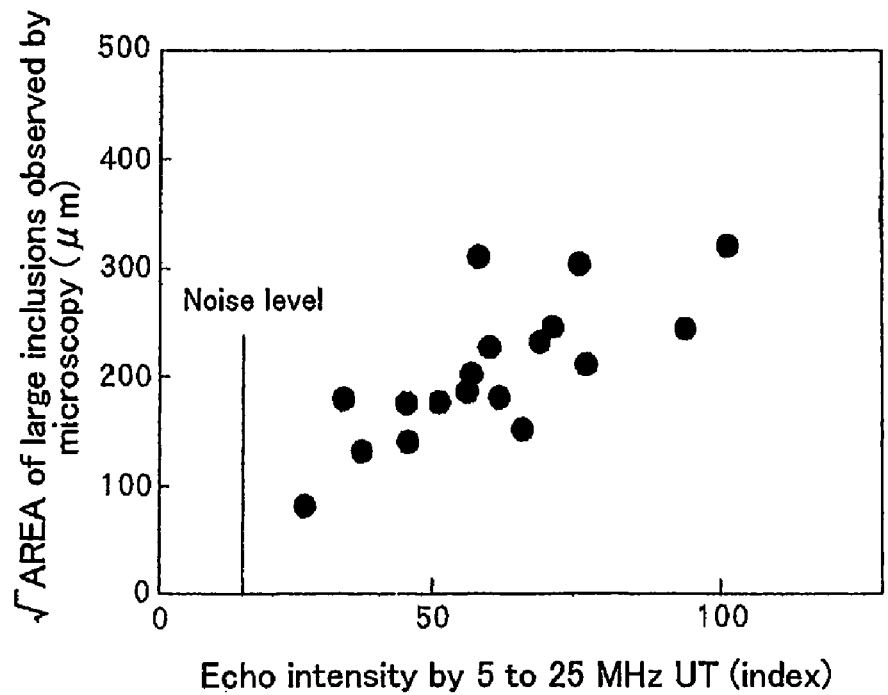
FIG. 3 is a diagram showing the relationship between the echo intensity from large inclusions at ultrasonic flaw detection testing at a flaw detection frequency of 5 to 25 MHz as demonstrated by the method for evaluating reliability of steel of the present embodiment, and $\sqrt{AREA}$ of the large inclusions observed by microscopy.

FIG. 3 shows the relationship between the echo intensity from large inclusions as demonstrated by an ultrasonic flaw detector operated at a frequency of 5 to 25 MHz (referred to as "5 to 25 MHz UT," hereinafter) according to the method of the present invention for evaluating the reliability of steel, and $\sqrt{AREA}$ of the large inclusions observed by microscopy. The detection by the 5 to 25 MHz UT provides the reliability for the frequency of appearance of large inclusions in the order of 100 μm or more in size.

We now describe the procedure of ultrasonic flaw detection testing in terms of (1) preparation of test specimen, (2) ultrasonic flaw detection, and (3) evaluation.

(1) Preparation of Test Specimen

Figure 4:
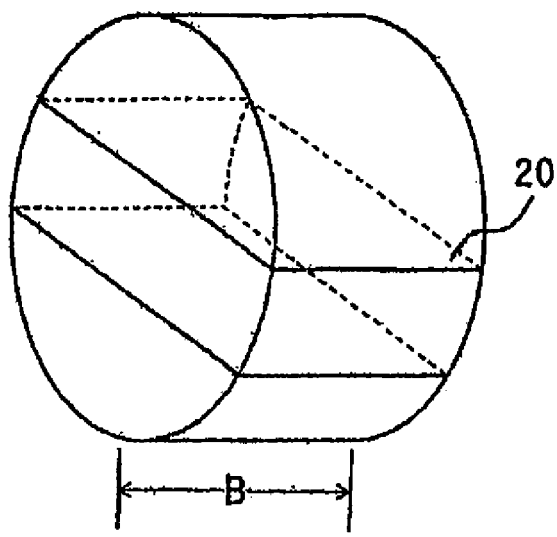
FIG. 4 is a perspective view showing a test specimen for the ultrasonic flaw detection testing according to the present embodiment.
Figure 5A:
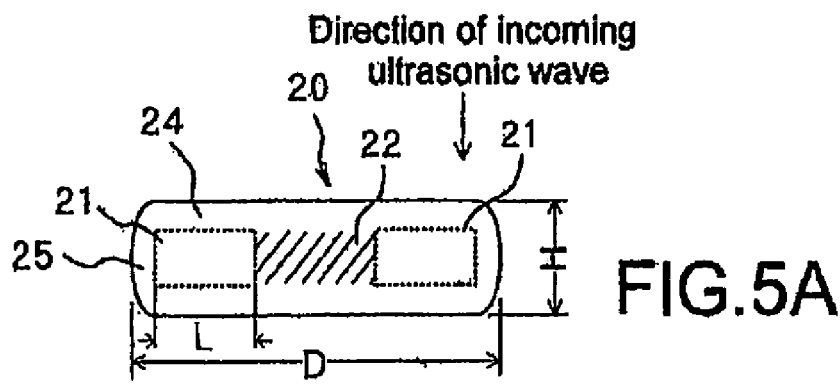
FIG. 5A is a cross-sectional front view of a test specimen shown in FIG. 4.
Figure 5B:
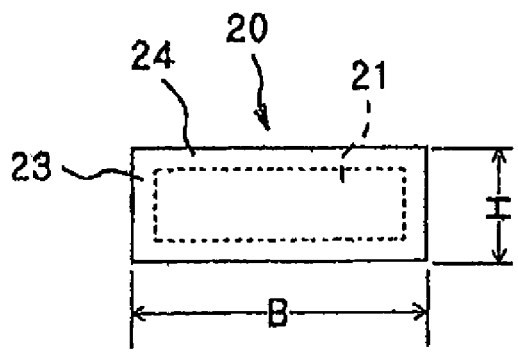
FIG. 5B is a side view of a test specimen shown in FIG. 4.

FIG. 4 is a perspective view of a test specimen of the present embodiment. FIG. 5A is a cross-sectional front view of the test specimen shown in FIG. 4. FIG. 5B is a side view of the test specimen shown in FIG. 4.

As shown in FIG. 4, a cylindrical billet having a rolling and/or forging ratio of 6 or higher is first prepared so as to compress porosities and increase the detection accuracy of inclusions. The billet is then cut into short cylinders with a predetermined width (B). A block with a predetermined height (H) is then cut out from the cylinder, as shown with the solid line in FIG. 5. This block is sequentially milled (crude working), normalized or annealed, and polished to make a test specimen 20 having predetermined dimensions.

An evaluation region 21 is the region other than the "porosity" region 22, peripheral region 25, non-sensitive region 24, and end regions 23. Large inclusions present in the evaluation region 21 are detected and evaluated.

(2) Ultrasonic Flaw Detection Testing

Figure 6:
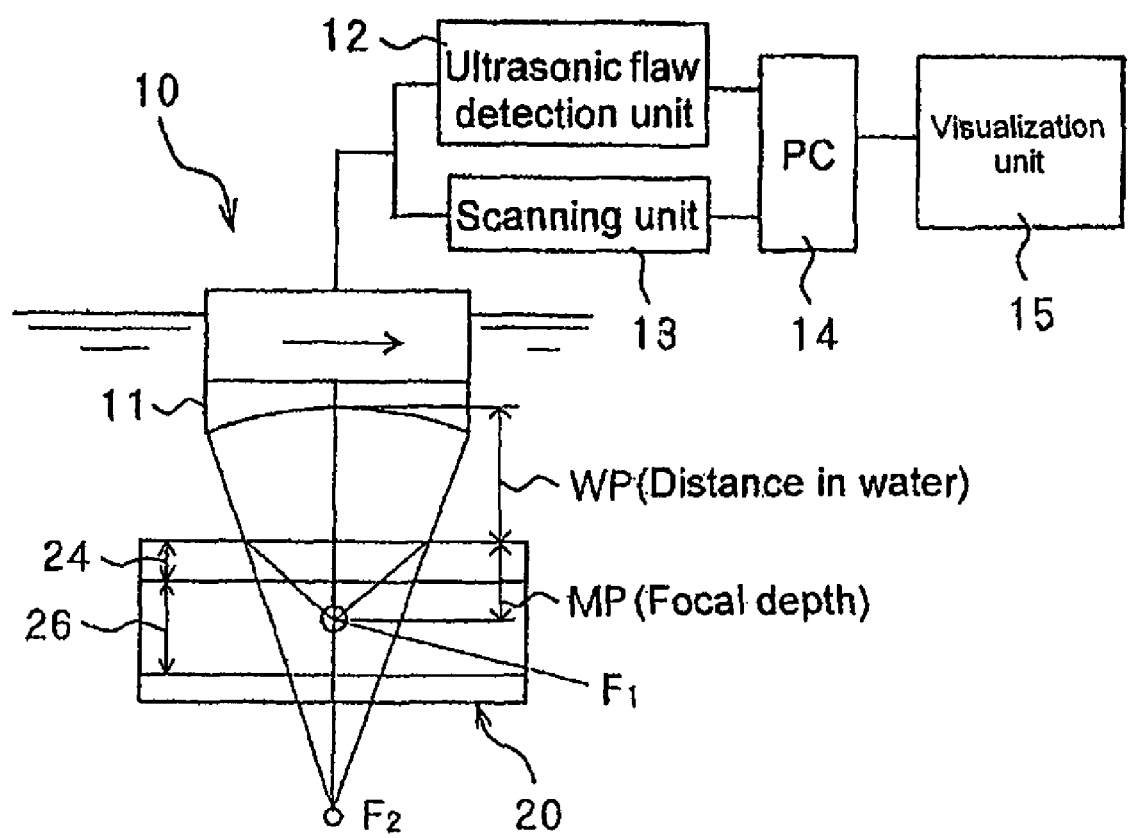
FIG. 6 is a schematic diagram of a water-immersed ultrasonic flaw detector of the present embodiment.

FIG. 6 is a schematic diagram of a water-immersed ultrasonic flaw detector. The water-immersed ultrasonic flaw detector denoted by the reference numeral 10 includes a point focused-type probe 11, an ultrasonic flaw detection unit 12, a scanning unit 13, a personal computer (PC) 14 equipped with a microprocessor, and a visualization unit 15.

The water-immersed ultrasonic flaw detector 10 is operated at a flaw detection frequency of 5 to 25 MHz and uses a standard test specimen (STB-A22 Standard Test Block mentioned in JIS Z2345 (standard test specimen for ultrasonic flaw detection test)) to calibrate the sensitivity. The reference sensitivity of the water-immersed ultrasonic flaw detector 10 is adjusted such that the maximum echo intensity from an artificial defect (φ1.5 mm flat bottom hole) of the standard specimen has a predetermined value (approx. 80%). The sensitivity is then increased by a particular amount (approx. 20 dB) for flaw detection.

The test specimen 20 is set in a water tank, and the sensitivity, the focal point depth beneath the specimen surface, and the detection range 26 are entered in the PC 14. The probe 11 is then scanned at a predetermined pitch to determine the number, position and size of inclusions.

(3) Evaluation

A sample (a steel product) is determined to be acceptable when the number of large inclusions in a specimen from the sample with a $\sqrt{AREA}$ value of greater than 100 μm in 10 kg converted evaluation weight is less than a predetermined number. The number of inclusions in 10 kg converted evaluation weight is converted from the number of inclusions in total evaluation weight (i.e., Total weight of evaluated range× number of specimens. The term has the same definition hereinafter.).

The above-described example enables detection/evaluation of large inclusions in steel and thereby makes it possible to obtain high-reliability steel that contains few or no large inclusions with a $\sqrt{AREA}$ value of greater than 100 μm that can lead to an accidental decrease in the rolling contact fatigue life.

The flaw detection frequency used in this embodiment was in the range of 5 to 25 MHz because ultrasound with a frequency lower than 5 MHz cannot effectively detect the desired large inclusions, while ultrasound with a frequency higher than 25 MHz is readily attenuated in steel such that large flaw detection volume cannot be achieved.

The detection system used in this embodiment was water-immersed ultrasonic flow detection system. This is because unlike the direct contact system, the water-immersed ultrasonic flow detection system can ensure stable acoustic coupling during scanning by probe, is hardly affected by the surface of test specimen, and enables stable and automatic flaw detection. In this system, the probe used was of the point focused-type because of the higher detectability of the probe as compared to the flat-type or linefocus-type probes.

A larger beam diameter of the flaw detection beam at its focal point permits a larger scanning pitch of flaw detection, allowing fast measurement. This however causes a decrease in the ability of the system to detect inclusions. For this reason, the probe preferably has a beam diameter of 0.5 to 3.0 mm at its focal point and the flaw detection is preferably carried out by taking advantage of the focal area (detection range) of −6 dB echo intensity (more preferably −3 dB) in the direction of depth to ensure better detectability.

The evaluation region of a sample specimen is a region that extends from 90% of the outer dimension D (=billet diameter. The term has the same definition hereinafter.) to just outside of the "porosity" region. This is because inclusions are more likely to be detected in the mid-region. Since the "porosity" region can vary in size depending on the type of steel and conditions of production, the evaluation region is preferably extended as far as the boundary of the "porosity" region to approximate the actual distribution of inclusions. In this example, the "porosity" region is the region inside 40% of the outer dimension D that contains the center of the test specimen. The figure 40% is determined assuming that a billet specified in JIS SUJ2 (rolling and/or forging ratio=8.5) is used and may thus vary depending on the type of steel: The porosity region is 20% of the outer dimension D for a billet specified in JIS SCM420 (JIS G 4105) (rolling and/or forging ratio=8.5) and 30% of the outer dimension D for a billet specified in JIS S53C (JIS G 4051) (rolling and/or forging ratio=8.5).

While the total evaluation weight used in this embodiment was 10 kg, it may be any amount in the order of kg that can ensure fast testing and high reliability of evaluation.

The test specimens are preferably normalized or annealed after milling to achieve fine and uniform micro-structure and improve their mechanical property. The specimens are also preferably flat-polished to further decrease the transmission loss of ultrasound.

The sensitivity of the 5 to 25 MHz UT procedure is adjusted so that the inclusions with a $\sqrt{AREA}$ value of 100 µm can be detected at a particular echo intensity. A sample (a steel product) is determined to be highly reliable when the number of inclusions (in specimens from the sample) that are detected at higher echo intensity than the predetermined echo intensity is 10 or less (in 10 kg converted evaluation volume). The sensitivity is preferably calibrated so that the $\phi$100 µm inclusions at the in-steel focal point of ultrasonic beam can be detected at a particular echo intensity. The sensitivity is indirectly calibrated by using artificial defects to simulate inclusions or the plot (calibration curve) shown in FIG. 3 since detection of $\phi$100 µm inclusions (natural defects) is difficult in practice.

According to this procedure, the frequency of appearance of cluster inclusions, massive inclusions and other large inclusions that follow the inclusion distribution different from the small- or medium-sized inclusions' distribution can be directly determined by the flaw detection in the order of kg. This significantly increases the reliability of supply materials in designing actual parts weighing in kg or less order.

The number of inclusions is preferably 2 or less (in 10 kg converted evaluation weight) and more preferably 0 (in 10 kg converted evaluation weight) since the evaluation by the present inventors has revealed that the frequency of appearance of large inclusions appearing in the rolling contact surface of actual parts becomes small, as does the frequency of accidental short life, when the number of large inclusions is less than the above-specified value.

It is preferred that a point focused-type probe having an ultrasonic beam diameter at the in-steel focal point of 0.5 to 3.0 mm, preferably 0.5 to 1.5 mm, is used and the focal length of the probe in water is in the range of 70 to 180 mm, preferably 120 to 180 mm. It is also preferred that the evaluation using the results of ultrasonic flaw detection is carried out by disregarding the "porosity" region of sample specimens and by using a total evaluation weight of 1 to 10 kg, preferably 5 to 10 kg.

Too small a beam diameter results in a decreased operability, whereas too large a beam diameter decreases the accuracy of measurement. While the practical beam diameter of the 15 MHz UT is 1 mm, it may be as large as 3.0 mm in theory. The preferred range of the focal length in water for the 15 MHz UT is determined to be from 70 to 180 mm since the detectability of the 15 MHz UT is improved when the focal length in water is about 150 mm and the in-steel focal depth is about 20 mm. The total evaluation weight is determined to be 1 to 10 kg in view of the balance between the inspection efficiency and large volume inspection.

We now describe in detail high-reliability steel of the present invention. The high-reliability steel of the present embodiment is a steel having a high reliability in terms of the inclusions present therein, the steel obtained through the selection by an inspection procedure characterized in that the inclusions of approximately 100 µm or less in maximum inclusion size are evaluated by microscopy combined with the extreme-value statistical analysis; the inclusions of approximately 100 µm or greater in maximum inclusion size are evaluated by the ultrasonic flaw detection testing performed at a frequency of 5 to 25 MHz; and the reliability of the steel is evaluated based on the combined results of the extreme-value statistical analysis applied to the results of the microscopy and the ultrasonic flaw detection testing.

Since we have already described the evaluation by microscopy combined with the extreme-value statistical analysis and the evaluation by the ultrasonic flaw detection testing and the evaluation of the total reliability over the entire size range of inclusions for use with the high-reliability steel of the present embodiment, the same description will not be repeated here. The high-reliability steel of the present embodiment is a steel for which total reliability over the entire size range of inclusions has been ensured.

In performing the evaluation by microscopy combined with the extreme-value statistical analysis to obtain the high-reliability steel of the present embodiment, it is preferred that a sample (a steel product) is determined to be highly reliable when the largest inclusion size ($\sqrt{AREAmax}$) estimated by the extreme-value statistical analysis with the standard inspection area of 80 mm$^2$ or larger and the estimation area of 30,000 mm$^2$ is 50 µm or less.

It is further preferred that in performing the evaluation by microscopy combined with the extreme-value statistical analysis to obtain the high-reliability steel of the present embodiment, a sample (a steel product) is determined to be highly reliable when the largest inclusion size ($\sqrt{AREAmax}$) estimated by the extreme-value statistical analysis with the standard inspection area of 80 mm$^2$ or larger and the estimation area of 30,000 mm$^2$ is 30 µm or less.

In performing the evaluation by microscopy combined with the extreme-value statistical analysis to obtain the high-reliability steel of the present invention, it is preferred that oxide, sulfide, and nitride inclusions are individually evaluated.

In performing the evaluation by ultrasonic flaw detection testing at a frequency of 5 to 25 MHz to obtain the high-reliability steel of the present embodiment, it is preferred that the flaw detection sensitivity is adjusted so that the inclusions of 100 µm in size can be detected at a predetermined echo intensity and a sample (a steel product) is determined to be highly reliable when the number of inclusions (in specimens from the sample) detected at the predetermined echo intensity or higher is 10 or less in the converted evaluation weight of 10 kg.

It is further preferred that in performing the evaluation by ultrasonic flaw detection testing at a frequency of 5 to 25 MHz to obtain the high-reliability steel of the present embodiment, the flaw detection sensitivity is adjusted so that the inclusions of 100 μm in size can be detected at a predetermined echo intensity and a sample (a steel product) is determined to be highly reliable when the number of inclusions (in specimens from the sample) detected at the predetermined echo intensity or higher is 2 or less in the converted evaluation weight of 10 kg.

It is still further preferred that in performing the evaluation by ultrasonic flaw detection testing at a frequency of 5 to 25 MHz to obtain the high-reliability steel of the present embodiment, the flaw detection sensitivity is adjusted so that the inclusions of 100 μm in size can be detected at a predetermined echo intensity and a sample (a steel product) is determined to be highly reliable when the number of inclusions (in specimens from the sample) detected at the predetermined echo intensity or higher is 0 in the converted evaluation weight of 10 kg.

It is preferred that in performing the evaluation by ultrasonic flaw detection testing at a frequency of 5 to 25 MHz to obtain the high-reliability steel of the present embodiment, a point focused-type probe having an ultrasonic beam diameter at the in-steel focal point of 0.5 to 3.0 mm is used and the focal length of the probe in water is in the range of 70 to 180 mm. It is also preferred that the evaluation using the results of ultrasonic flaw detection testing is carried out by disregarding the "porosity" region of sample specimens and by using a total evaluation weight of 1 to 10 kg.

Example

The method for evaluating the reliability of steel in accordance with the embodiment of the present invention will now be described in further detail with reference to examples, which are not intended to limit the scope of the invention in any way.

Figure 8:
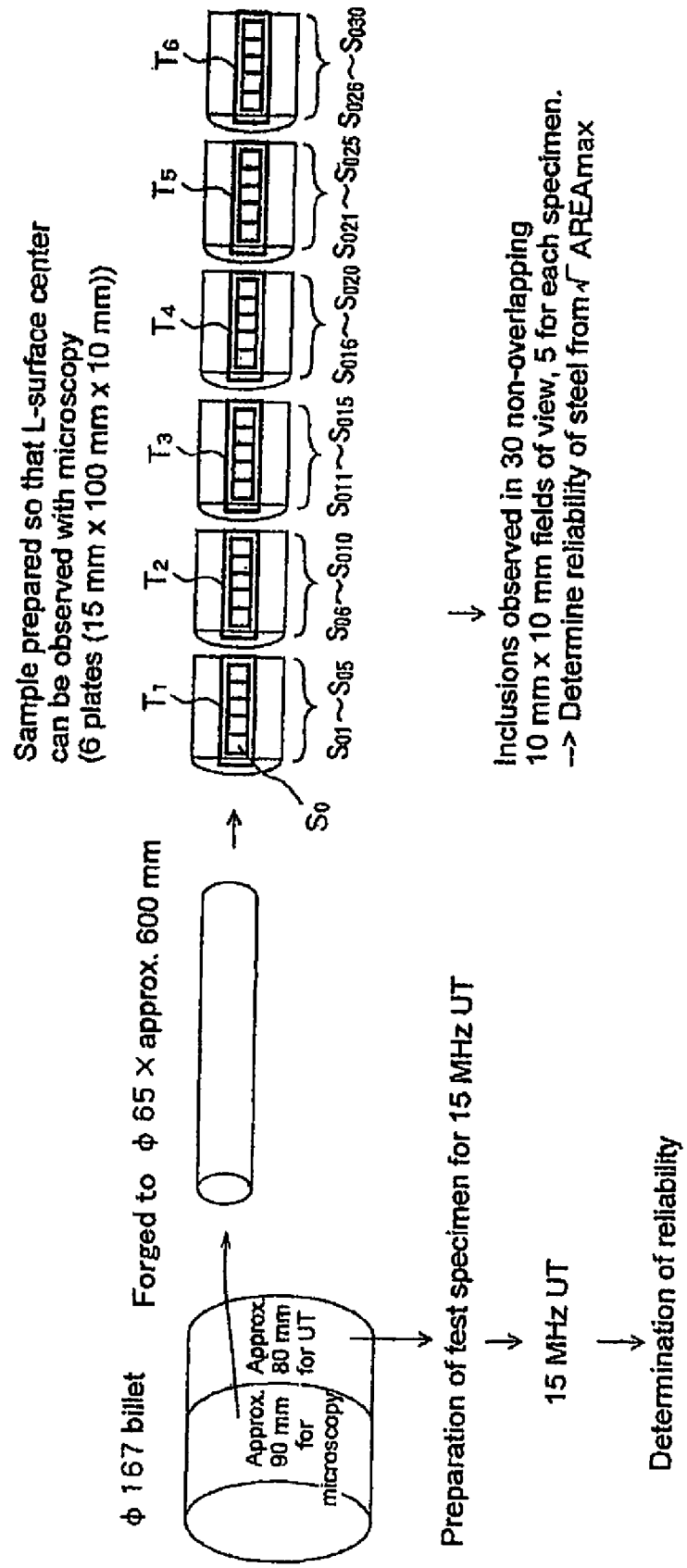
FIG. 8 is a diagram showing the course of a process from the preparation of test specimens for the reliability test to the reliability evaluation in the method for evaluating reliability of steel of the present example.

FIG. 8 is a diagram showing the course of a process from the preparation of test specimens for the reliability test to the reliability evaluation of the embodiment.

A φ167 mm billet produced from a vertical continuous casting material (JIS SUJ2, [O]≦10 ppm) is divided into a block for microscopy analysis and a block for 15 MHz UT analysis. The block for microscopy analysis is forged to φ65 mm and test pieces (6 plates $T_1$ through $T_6$ each sized 15 mm×100 mm×10 mm) are prepared from the core of the block for microscopy analysis for L-surface observation. The central region of the L-surface, which preferably contains the peripheral part of the central axis of the sample, is observed by microscopy. The 15 mm×100 mm surface of each of the 6 plates is observed by microscopy for the presence of inclusions in 5 non-overlapping 10 mm×10 mm fields of view (designated as $S_{0n}$ ($S_{01}$ through $S_{030}$ in total). Test specimens (for L-surface observation) are also prepared from the block for 15 MHz UT analysis.

The term "L-surface" as used herein refers to a surface parallel to the direction of rolling or extend forging of the product.

Figure 7:
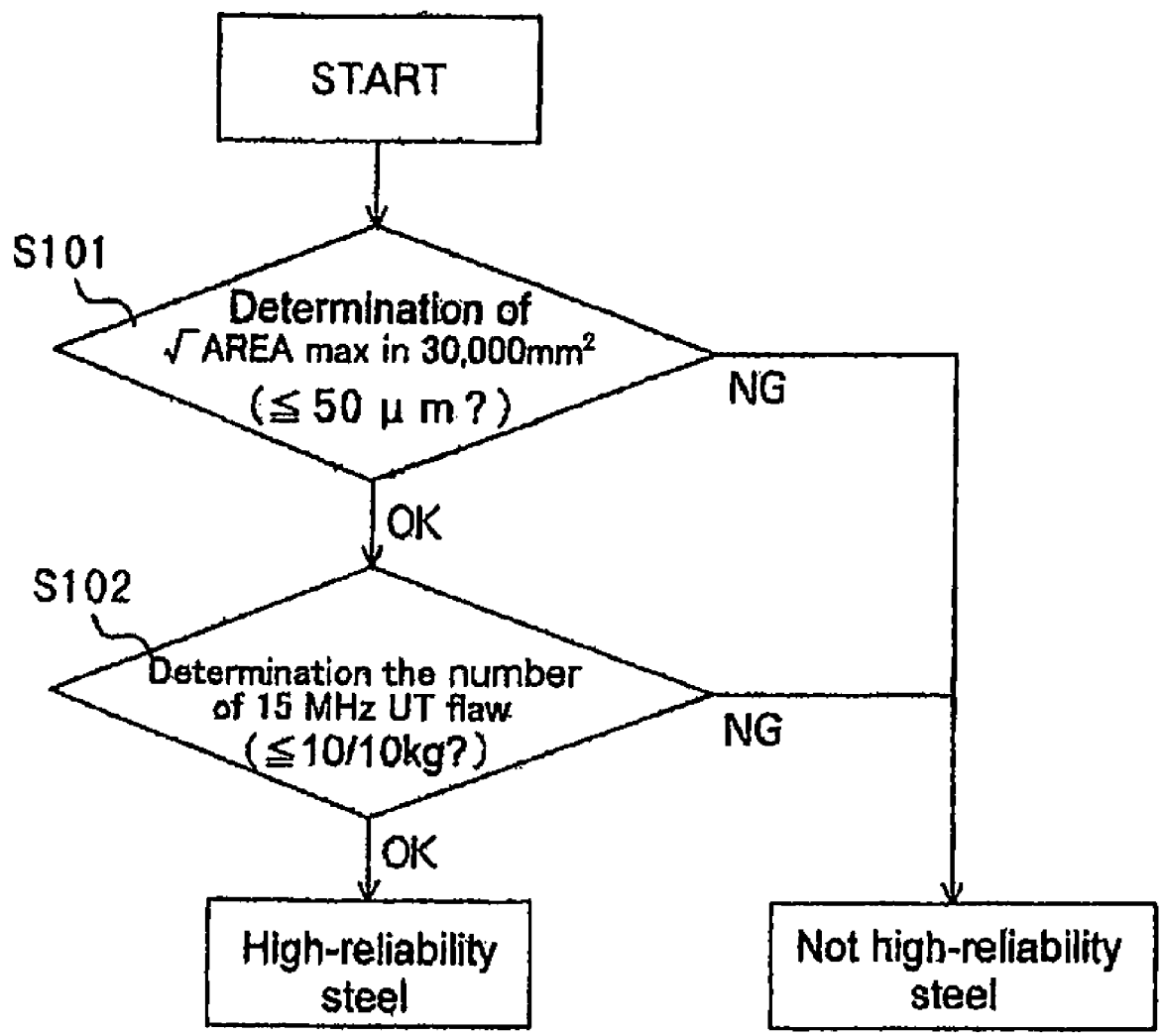
FIG. 7 is a flow chart of a method for evaluating reliability of steel according to an example.

FIG. 7 is a flow chart of the method of the present invention for evaluating the reliability of steel.

In Step 101 (In the figure, each step is indicated by S), samples are evaluated by performing the microscopy combined with extreme-value statistical analysis with the standard inspection area $S_0=100$ mm², the number of $S_{0n}=30$, and the estimation area $S=30,000$ mm² to determine the √AREAmax value. The standard used in this evaluation is √AREAmax≦50 μm.

In Step 102, samples are evaluated by 15 MHz UT with total evaluation weight of 1 to 10 kg. In this step, the inclusions detected at an echo intensity that corresponds to √AREA value of 100 μm or higher intensities are counted. The count is converted to the number of inclusions in 10 kg evaluation volume. Specimens are rated on the basis of the number of inclusions detected at particular echo intensity, e.g., 0 inclusion at 80% or higher echo intensities, or 2 or fewer inclusions at 30% or higher echo intensities.

Alternatively, samples may be rated on the basis of the threshold determined by the 15 MHz UT analysis. For example, samples that have passed the test by the microscopy combined with extreme-value statistical analysis may be rated as A, B, C or "not-reliable" with "high-reliability steel A" corresponding to 0 inclusions detected by 15 MHz UT (in 10 kg evaluation volume), "high-reliability steel B" corresponding to more than 0 to 2 inclusions detected by 15 MHz UT (in 10 kg evaluation volume), "high-reliability steel C" corresponding to more than 2 to 10 inclusions detected by 15 MHz UT (in 10 kg evaluation volume), and "not-reliable steel" corresponding to more than 10 inclusions detected by 15 MHz UT (in 10 kg evaluation volume).

In this example, a sample (a steel product) with 10 or fewer inclusions detected at predetermined or higher echo intensities (in 10 kg evaluation volume in specimens from the sample) is determined to be highly reliable.

It should be appreciated that the threshold for the extreme values (√AREAmax) may also be varied to meet the requirements of users.

Table 1 shows the results of the evaluation performed according to the method for evaluating the reliability of steel of the present example.

TABLE 1

| Sample No | √AREAmax [μm] (S101) | The number of inclusions detected by 15 MHz UT (inclusions/10 kg) (S102) | Determination of pass/failure of product |
|---|---|---|---|
| 1 | 40.4 | 12 | Failure |
| 2 | 17.4 | 0 | Pass |
| 3 | ▓▓ | 8 | Failure |
| 4 | 18.1 | 5 | Pass |
| 5 | 30.9 | 5 | Pass |
| 6 | ▓▓ | ▓▓ | Failure |
| 7 | 49.3 | 3 | Pass |
| 8 | 36.5 | 0 | Pass |
| 9 | 11.4 | 1 | Pass |
| 10 | ▓▓ | ▓▓ | Failure |

TABLE 1-continued

| Sample No | √AREAmax [µm] (S101) | The number of inclusions detected by 15 MHz UT (inclusions/10 kg) (S102) | Determination of pass/ failure of product |
|---|---|---|---|
| 11 | 102.4 | 0 | Failure |
| 12 | 80.3 | 3 | Failure |
| 13 | 46.8 | 1 | Pass |
| 14 | 74.0 | 15 | Failure |
| 15 | 29.6 | 30 | Failure |

In this example, a sample with a √AREAmax value of more than 50 µm is determined to be defective. A sample with a √AREA value of 50 µm or less is determined to be defective if the number of inclusions in 10 kg detected by the 15 MHz UT is greater than 10. A sample is determined to be defective if either of the two conditions is not met. Thus, the method of the present example can properly evaluate both large microinclusions of approximately 100 µm or less in size and large inclusions of approximately 100 µm or more in size. As a result, the total reliability can be determined over the entire size range of inclusions.

The high-reliability steel according to the embodiment of the present invention will now be described in further detail with reference to examples, which are not intended to limit the scope of the invention in any way.

Figure 9:
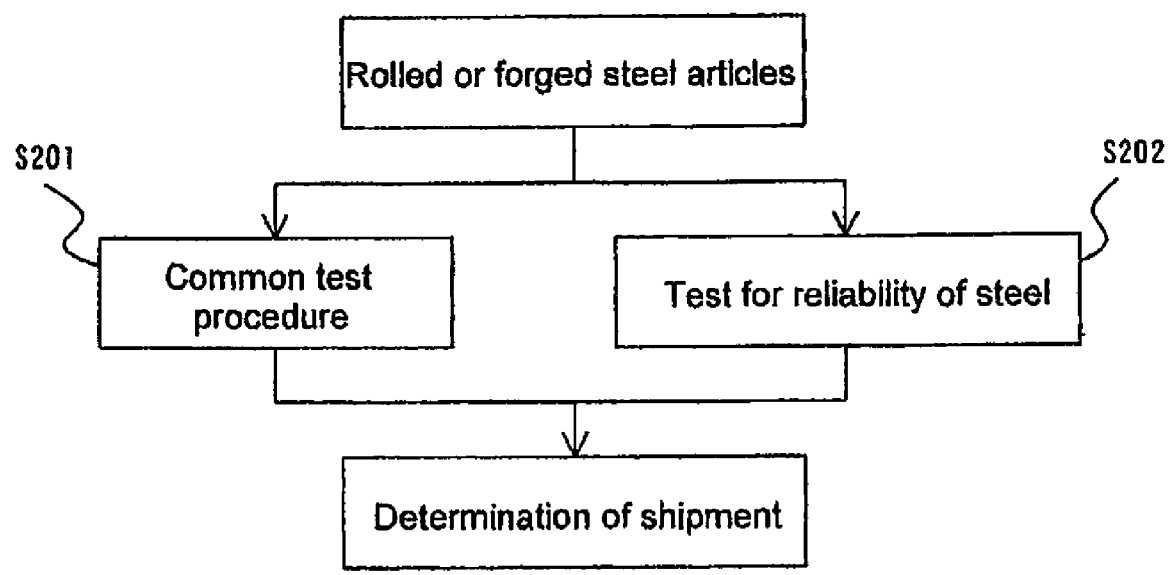
FIG. 9 is a chart showing one inspection procedure for high-reliability steel according to the present example.

FIG. 9 is a chart showing one inspection procedure for high-reliability steel according to the present example.

A φ167 mm billet produced from a vertical continuous casting material (JIS SUJ2, [O]≦10 ppm) is first tested by a common procedure for internal quality and surface quality (Step 201). Subsequently, the billet is tested by the method for evaluating the reliability of steel of the present example (Step 202). The inspection procedure of the reliability of steel in Step 202 is the same as the flow of the method for evaluating the reliability of steel of the present example described with reference to FIG. 7 (Steps 101 and 102).

Only sample that have passed the common test (Step 201) may be subjected to the test of the present example (Step 202). A qualified product for shipment is determined based on the results of the two tests.

Table 2 shows the criteria for selecting highly reliable steel by the inspection procedure which performs the evaluation of reliability of steel in accordance with the present example.

TABLE 2

| Lot No. | Determination by common test procedure (Step 201) | Determination by the method for evaluating reliability of steel according to the present example (Step 202) | Determination of shipment as high-reliability steel |
|---|---|---|---|
| 1 | Pass | Pass | Pass |
| 2 | Pass | Failure | Failure |
| 3 | Failure | Pass | Failure |
| 4 | Failure | Failure | Failure |

A "Pass" in the table indicates that the sample has passed the test and a "Failure" indicates that the sample has failed the test. As shown, the high-reliability steel of the present example is tested not only by the common inspection procedure (Step 201), but also by the inspection procedure in accordance with the method for evaluating the reliability of steel of the present example (Step 202), so that it is determined to be a highly reliable product qualified for shipment.

While preferred embodiments have been described, it is to be understood that modification and variation of the present invention may be made without departing from scope of the following claims.

The invention claimed is:

1. A method for evaluating reliability of steel, the method comprising:
    evaluating an $L_{10}$ life of steel by evaluating inclusions of approximately 100 µm or less in maximum inclusion size by microscopy combined with extreme-value statistical analysis;
    evaluating an accidental short life of the steel by evaluating inclusions of approximately 100 µm or greater in maximum inclusion size by a ultrasonic flaw detection testing performed at a frequency of 5 to 25 MHz; and
    evaluating the reliability of the steel based on the results of the extreme-value statistical analysis applied to the results of the microscopy and the results of the ultrasonic flaw detection testing performed at a frequency of 5 to 25 MHz combined.

2. The method for evaluating reliability of steel according to claim 1, further comprising:
    determining the steel to be highly reliable by the evaluation by microscopy combined with extreme-value statistical analysis when the largest inclusion size estimated by the extreme-value statistical analysis for a standard inspection area S0 of 80 mm² or larger and an estimation area S of 30000 mm² is 50 µm or less.

3. The method for evaluating reliability of steel according to claim 1, further comprising:
    determining the steel to be highly reliable by the evaluation by microscopy combined with extreme-value statistical analysis when the largest inclusion size estimated by the extreme-value statistical analysis for a standard inspection area S0 of 80 mm² or larger and an estimation area S of 30000 mm² is 30 µm or less.

4. The method for evaluating reliability of steel according to claim 1, wherein the evaluation by microscopy combined with the extreme-value statistical analysis is individually applied to oxide, sulfide, and nitride inclusions.

5. The method for evaluating reliability of steel according to claim 1, wherein the evaluation by the ultrasonic flaw detection testing at a frequency of 5 to 25 MHz is performed at a sensitivity which detects inclusions having a size of 100 µm at a predetermined echo intensity, and
    wherein the steel is determined to be highly reliable when the number of inclusions detected at the predetermined echo intensity or higher echo intensities is 10 or less in 10 kg converted evaluation weight.

6. The method for evaluating reliability of steel according to claim 1, wherein the evaluation by the ultrasonic flaw detection testing at a frequency of 5 to 25 MHz is performed at a sensitivity which detects inclusions having a size of 100 µm at a predetermined echo intensity, and
wherein the steel is determined to be highly reliable when the number of inclusions detected at the predetermined echo intensity or higher echo intensities is 2 or less in 10 kg converted evaluation weight.

7. The method for evaluating reliability of steel according to claim 1, wherein the evaluation by the ultrasonic flaw detection testing at a frequency of 5 to 25 MHz is performed at a sensitivity which detects inclusions having a size of 100 µm at a predetermined echo intensity, and
wherein the steel is determined to be highly reliable when the number of inclusions detected at the predetermined echo intensity or higher echo intensities is zero in 10 kg converted evaluation weight.

8. The method according to claim 1, wherein performing the evaluation by the ultrasonic flaw detection testing at a frequency of 5 to 25 MHz includes:
using a point focused-type probe having an ultrasonic beam diameter at an in-steel focal point of 0.5 to 3.0 mm;
adjusting a focal length in water of the point focused-type probe to 70 to 180 mm; and
disregarding a porosity region of a sample specimen,
wherein a total evaluation weight is 1 to 10 kg.

9. A high-reliability steel having high reliability in terms of inclusions present therein, the steel being obtained by selection using an inspection process for evaluating reliability of steel including:
evaluating an $L_{10}$ life of steel by evaluating inclusions of approximately 100 µm or less in maximum inclusion size by microscopy combined with extreme-value statistical analysis;
evaluating an accidental short life of the steel by evaluating inclusions of approximately 100 µm or greater in maximum inclusion size by a ultrasonic flaw detection testing performed at a frequency of 5 to 25 MHz; and
evaluating the reliability of the steel based on the results of the extreme-value statistical analysis applied to the results of the microscopy and the results of the ultrasonic flaw detection testing performed at a frequency of 5 to 25 MHz combined.

10. The high-reliability steel according to claim 9, wherein the largest inclusion size of the steel is 50 µm or less, the largest inclusion size of the steel being estimated by the extreme-value statistical analysis for a standard inspection area S0 of 80 mm² or larger and an estimation area S of 30000 mm².

11. The high-reliability steel according to claim 9, wherein the largest inclusion size of the steel is 30 µm or less, the largest inclusion size of the steel being estimated by the extreme-value statistical analysis for a standard inspection area S0 of 80 mm² or larger and an estimation area S of 30000 mm².

12. The high-reliability steel according to claim 9, wherein the evaluation by microscopy combined with the extreme-value statistical analysis is individually applied to oxide, sulfide, and nitride inclusions.

13. The high-reliability steel according to claim 9, wherein the evaluation by the ultrasonic flaw detection testing at a frequency of 5 to 25 MHz is performed at a sensitivity which detects inclusions having a size of 100 µm at a predetermined echo intensity, and
wherein the steel has 10 or less inclusions in 10 kg converted evaluation weight, the number of inclusions in the steel being detected at the predetermined echo intensity or higher echo intensities.

14. The high-reliability steel according to claim 9, wherein the evaluation by the ultrasonic flaw detection testing at a frequency of 5 to 25 MHz is performed at a sensitivity which detects inclusions having a size of 100 µm at a predetermined echo intensity, and
wherein the steel has 10 or less inclusions in 10 kg converted evaluation weight, the number of inclusions in the steel being detected at the predetermined echo intensity or higher echo intensities.

15. The high-reliability steel according to claim 9, wherein the evaluation by the ultrasonic flaw detection testing at a frequency of 5 to 25 MHz is performed at a sensitivity which detects inclusions having a size of 100 µm at a predetermined echo intensity, and
wherein the steel has no inclusions in 10 kg converted evaluation weight, the number of inclusions in the steel being detected at the predetermined echo intensity or higher echo intensities.

16. The high-reliability steel according to claim 9, wherein the evaluation by the ultrasonic flaw detection testing at a frequency of 5 to 25 MHz includes:
using a point focused-type probe having an ultrasonic beam diameter at an in-steel focal point of 0.5 to 3.0 mm;
adjusting a focal length in water of the point focused-type probe to 70 to 180 mm; and
disregarding a porosity region of a sample specimen,
wherein a total evaluation weight is 1 to 10 kg.

* * * * *